United States Patent [19]
Govil et al.

[11] Patent Number: 5,154,922
[45] Date of Patent: Oct. 13, 1992

[54] COMPOSITIONS FOR TRANSDERMAL DELIVERY OF ESTRADIOL

[75] Inventors: Sharad K. Govil, Plantation; Dale Sterner, Pembroke Pines; Stephen Jones, Miami; Geraldine Kennedy, Plantation, all of Fla.

[73] Assignee: Schering Corporation, Kenilworth, N.J.

[21] Appl. No.: 675,936
[22] PCT Filed: Nov. 29, 1989
[86] PCT No.: PCT/US89/05288
   § 371 Date: May 7, 1991
   § 102(e) Date: May 7, 1991
[51] Int. Cl.⁵ .............................. A61F 13/02
[52] U.S. Cl. ...................... 424/448; 424/447; 424/449; 424/487
[58] Field of Search .............. 424/447, 448, 449, 487

[56] References Cited

U.S. PATENT DOCUMENTS

| | | | |
|---|---|---|---|
| 4,291,014 | 9/1981 | Keith et al. | 424/486 |
| 4,305,936 | 12/1981 | Klein | 424/242 |
| 4,557,934 | 12/1985 | Cooper | 514/159 |
| 4,559,222 | 12/1985 | Enscore et al. | 424/28 |
| 4,568,343 | 2/1986 | Leeper et al. | 604/896 |
| 4,624,665 | 11/1986 | Nuwayser | 604/307 |
| 4,666,441 | 5/1987 | Andriola et al. | 424/448 |
| 4,668,232 | 5/1987 | Cordes et al. | 604/897 |
| 4,685,911 | 8/1987 | Konno et al. | 604/897 |
| 4,695,465 | 9/1987 | Kigasawa et al. | 424/449 |
| 4,704,282 | 11/1987 | Campbell | 424/449 |
| 4,710,383 | 12/1987 | Dick | 424/449 |
| 4,746,515 | 5/1988 | Cheng | 424/449 |
| 4,764,379 | 8/1988 | Sanders | 424/449 |
| 4,788,062 | 11/1988 | Gale et al. | 424/449 |
| 4,842,864 | 6/1989 | Guillemet et al. | 424/448 |

FOREIGN PATENT DOCUMENTS

| | | |
|---|---|---|
| 147146 | 7/1985 | European Pat. Off. . |
| 250125 | 12/1987 | European Pat. Off. . |
| 3333240 | 3/1985 | Fed. Rep. of Germany . |
| 2547502 | 12/1984 | France . |
| 8602584 | 6/1987 | PCT Int'l Appl. . |
| 8707138 | 12/1987 | PCT Int'l Appl. . |
| 1470355 | 4/1977 | United Kingdom . |
| 2093694 | 9/1982 | United Kingdom . |
| 2158355 | 11/1985 | United Kingdom . |
| 2185187 | 7/1987 | United Kingdom . |

OTHER PUBLICATIONS

Bennet et al., J. Pharm. Pharmacol., 37 (1985) 298.
Cooper, J. Pharm. Sci., 73 (1984), 1153.
C.A., 109 (26):237062d.
C.A., 107 (10):83806u (J. Pharm. Pharmacology, 39 (7) pp. 535-546).
C.A., 109 (26): 237061c.

Primary Examiner—Thurman K. Page
Assistant Examiner—D. Gabrielle Phelan
Attorney, Agent, or Firm—Anita W. Magatti

[57] ABSTRACT

Solvent systems comprising oleic acid, linear alcohol lactate and either dipropylene glycol or N-methyl-2-pyrrolidine useful for preparing adhesive matrix and reservoir-type transdermal delivery devices for estradiol are disclosed.

13 Claims, No Drawings

COMPOSITIONS FOR TRANSDERMAL DELIVERY OF ESTRADIOL

"This application claims priority of International Application Number PCT/US89/05288, filed internationally on Nov. 29, 1989, which is a continuation-in-part application U.S. Ser. No. 07/278,625, filed Dec. 1, 1988, now abandoned.

SUMMARY OF THE INVENTION

The present invention relates to transdermal delivery of estradiol using a solvent system comprising oleic acid, linear alcohol lactate and either dipropylene glycol or N-methyl-2-pyrrolidone. Said solvent system may be used to prepare an adhesive matrix transdermal device or a reservoir transdermal device.

In particular, adhesive matrices can be prepared from vinyl acetate, acrylic, silicone or synthetic or natural rubber latex pressure sensitive adhesives. Where the transdermal device comprises a reservoir, the solvent system may be used to prepare a solution or a gel.

BACKGROUND

The use of estradiol in estrogen replacement therapy is well known, and in fact an estradiol transdermal system comprising estradiol and ethanol gelled with hydroxypropyl cellulose in a reservoir-type transdermal patch is commercially available from CIBA Pharmaceutical Company (ESTRADERM®).

Various patents and published applications also relate to transdermal estradiol systems. For instance, U.K. patent application 2,093,694 discloses co-administration of estradiol and ethanol to increase dermal penetration of the drug. Several other publications relate in general to enhancing dermal penetration of drugs and also specifically name estradiol; U.S. Pat. No. 4,658,343 to Leeper et al discloses the use of polyethylene glycol monolaurate as a penetration enhancer; U.K. patent application 2,158,355 to Sarpotdar et al disclose the similar use of a combination of propylene glycol and glycerin in specified ratios; and European patent application 147,146 to Tsuk discloses menthol as a penetration enhancer.

Other patent publications discloses the use of a matrix or gel for transdermally delivery estradiol: PCT publication WO87/07138 to Chien et al discloses estradiol microdispersed in a polymer (e.g. a silicone polymer) matrix; U.S. Pat. No. 4,668,232 to Cordes et al discloses a drug in a reservoir comprised of a polymer matrix composed of a rubber, an adhesive resin material, and a water-swellable polymer (e.g. a polysaccharide); U.S. Pat. No. 4,559,222 to Enscore et al discloses a mineral oil-polyisobutylene-colloidal silicon dioxide matrix useful for transdermal delivery of estradiol, among other drugs; German patent application 3,333,240 discloses estradiol dissolved in a gel, which gel is dispersed in a crosslinked silicone elastomer; French patent application 2,547,502 and U.S. Pat. No. 4,291,014 to Keith et al both disclose a transdermal matrix suitable for estradiol which comprises a polar plasticizer (e.g. polyethylene glycol), a polyvinyl alcohol and a polyvinyl pyrrolidone.

Still other patents relate to the more mechanical aspects of transdermal devices suitable for estradiol administration. European patent application 250,125 to Berry et al and U.K. patent application 2,185,187 to Campbell et al disclose drug-containing matrices incorporating fibers, which fibers absorb the active or impart flexibility to the device, respectively; U.S. Pat. No. 4,666,441 to Andriola et al discloses a transdermal device with multiple compartments to prevent uneven settling of the active in the patch when stored; and U.S. Pat. No. 4,624,665 to Nuwayser discloses microparticles of drug dispersed in a viscous material.

Effective transdermal administration of many drugs has been achieved using various skin penetration enhancers. Oleic acid has been reported to be a penetration enhancer; see Cooper, "Increased Skin Permeability for Lipophilic Molecules", *J. Pharm. Sci.*, 73, 1153 (1984), wherein the use of varying concentrations of oleic acid in a polar solvent such as a diol (especially propylene glycol) enhanced the penetration of salicylic acid. U.S. Pat. No. 4,305,936 discloses a solution for topical or local application of a corticosteroid comprising a clyceral ester of a fatty acid of 6 to 22 carbon atoms, an alkanol cosolvent (e.g., dipropylene glycol), and a "suitable auxiliary adjuvant", e.g., oleic acid. PCT Application No. US86/02584 discloses enhanced penetration of mouse skin by estradiol in a carrier comprising 2-ethyl-1,3-hexane diol and oleic acid.

Disclosures relating to skin penetration enhancement with N-methyl-2-pyrrolidone (m-pyrol) include Bennett et al., "Optimization of bioavailability of topical steroids: non-occluded penetration enhancers under thermodynamic control", *J. Pharm. Pharmacol.*, 37, 298 (1985), wherein both m-pyrol and a combination of oleic acid and propylene glycol were reported to increase steroid (betamethasone 17-benzoate) bioavailability. U.S. Pat. No. 4,557,934 to Cooper discloses a combination of Azone and m-pyrol or a $C_3$–$C_4$ diol to enhance penetration of a variety of drugs, although estradiol is not specifically mentioned.

DETAILED DESCRIPTION

We have surprisingly found that the use of specific solvent systems not only serves to dissolve estradiol in a pressure sensitive polymeric adhesive matrix suitable for a transdermal device, but also promotes diffusion of estradiol through and out of the matrix and acts as a skin penetration enhancer to provide optimum, controlled transdermal flux through human skin. The transdermal delivery devices of the present invention therefore includes both adhesive matrix and reservoir transdermal devices comprising either of two specific solvent systems which have found to be especially useful for preparing the devices and for administering estradiol. One solvent system comprises dipropylene glycol (DPG), oleic acid and linear alcohol lactate and the second solvent system comprises m-pyrol, oleic acid and linear alcohol lactate. The DPG solvent system is preferred.

Adhesive drug matrices of the present invention may be prepared from a polymer mixture (i.e. a polymer blend) comprising, in addition to estradiol, a pressure sensitive polymeric adhesive and the solvent components listed above, a crosslinking agent, a polymer thickener to adjust viscosity, and one or more processing solvents such as water and an alcohol such as ethanol. The concentrations of the components depend on whether they are determined before of after curing, since during the drying and curing processes the solvents largely evaporate. The concentrations which follow are calculated as a w/w percentage. On a "wet" basis, the adhesive concentration is about 60 to about 80%, preferably about 70 to about 75%, the crosslinking agent is present at about 0.1 to about 0.5%, preferably about 0.3%, and the thickener is present at about 0.5 to about 1.5%, preferably about 1% or as necessary to adjust viscosity. The processing solvents represent about 10 to about 20% of the wet mixture, with typically about 5 to about 10% being water and about 2 to about 10% being alcohol.

For the DPG solvent system, the concentration range ("wet" basis) is about 1 to about 20% DPG, about 1 to about 20% oleic acid and about 1 to about 10% linear alcohol lactate (a $C_{12}$–$C_{15}$ alcohol lactate, e.g. Ceraphyl-41 from Van Dyk, Division of Mallinckrodt, Inc., Belleville, N.J.), preferably about 2 to about 10%, especially about 5% DPB, about 2to about 5%, especially about 3% oleic acid, and about 2 to about 5%, especially about 3% linear alcohol lactate. The m-pyrol solvent system comprises about 1 to about 20% m-pyrol, about 1 to about 20% oleic acid and about 1 to about 10% linear alcohol lactate, preferably about 2 to about 10% especially about 5% m-pyrol, about 2 to about 5%, especially about 3% oleic acid and about 2 to about 5% especially about 3% linear alcohol lactate.

Concentration ranges of the components in a cured matrix (i.e., "dry" basis) are about 70 to about 90% pressure sensitive adhesive, about 0.1 to about 0.5% crosslinker, about 1 to about 2% thickener, about 2.5 to about 5% linear alcohol lactate, about 2.5 to about 5% oleic acid, and about 5 to about 10% DPG or m-pyrol.

For a reservoir-type device, concentration ranges similar to the "wet" basis range above may be used, since the final transdermal device preferably comprises an adhesive layer with the same components as described above, except that the adhesive layer is separated from the estradiol solution by a polymer membrane. If, however, a different type of device is used (e.g. the adhesive is applied only around the edge of a device, thereby using proportionately less adhesive), the concentration percentages for the estradiol solution components are calculated on a different basis since the adhesive, crosslinking agent, thickener, and processing solvents are not present. Concentration ranges for the solvent system in an estradiol solution per se are about 20% to about 60% m-pryol or DPG, preferably about 40% to about 50%, especially about 45% DPG or m-pyrol; about 10% to about 50% oleic acid, preferably about 15 to about 25%, especially about 23% oleic acid; and about 10 to about 40% linear alcohol lactate, preferably about 15 to about 25%, especially about 23% linear alcohol lactate.

As used herein in the specification, the term "estradiol" includes estradiol and the pharmaceutically acceptable esters thereof. The concentration of estradiol in an adhesive matrix of the present invention similarly depends on whether it is measured "wet", i.e., in the polymer blend before curing, or "dry", i.e. after curing. When "wet", estradiol is present at about 0.5 to about 5%, preferably about 1%, and when "dry" at about 1 to about 10%, preferably about 2%. In a reservoir device comprising a preferred adhesive layer as described above, estradiol is present at a concentration of about 0.5 to about 5%, while estradiol concentration in the solvent system alone is about 5% to about 10%, preferably about 8 to about 15%, especially about 9%.

Pressure sensitive polymeric adhesives suitable for preparing matrices of the present invention include pharmaceutically acceptable acrylic, vinyl acetate, silicone and synthetic or natural rubber adhesives. For example, acrylic adhesives such as RA 2484, RA 2333, RA 2397, RA 3011 from Monsanto Co. are appropriate.

Other acrylic adhesives, such as Durotak, manufactured by Morton Thiokol, Inc., and Neocryl XA5210 by Polyvinyl Chemicals, Ltd. may be utilized.

Vinyl acetate adhesives include Flexbond 149 and Flexbond 150 from Air Products.

Numerous silicone based adhesives may be used, such as Q72929, Q27406, X72920 and 355, each manufactured by Dow-Corning.

Natural and synthetic rubbers include polyisobutylenes, neoprenes, polybutadienes and polyisoprenes.

The adhesives may be used singly or combined for use in the patch.

A crosslinking agent may be added to facilitate curing, for example Aerotex Resin 3730 (American Cyanamid) and a thickener may be added to adjust the viscosity of the polymer mixture to about 6000–10,000 cps for coating on a backing material (the initial viscosity is about 3000 cps). The thickener can be acrylic polymer thickener such as AMSCO 6038A (Unocal).

For adhesive-matrix devices, the polymer blend is applied to a suitable backing material impermeable to estradiol or the other components of the polymer blend. The backing materials, which are preferably water resistant and can be occlusive or nonocculsive, can be selected from such materials as foam, metal foil, polyester, low density polyethylene, copolymers of vinyl chloride and polyvinylidene chloride (e.g. Saran), and laminates thereof. A typical foam backing is a polyethylene closed cell radiation cross-linked foam such as Volar (Voltek, Division of Sekisui America Corp., Lawrence, Mass.).

Where the transdermal device is a reservoir-type device, either solvent system described above can be used to form an estradiol solution to fill the reservoir, or about 0.1 to about 2%, preferably about 0.5% of a gelling agent such as hydroxypropyl cellulose can be added to form a gel. The solution or gel is retained in the reservoir by a suitable rate-controlling membrane such as an ethylene-vinyl (EVA) copolymer membrane (e.g. 1%–20% vinyl acetate), which membrane preferably has a face layer of a pressure sensitive adhesive as described above. Backing materials for reservoir-type patches are similar to those described above for adhesive matrix-type devices.

Both adhesive matrix and reservoir devices preferably contain a release linear impermeable to the drug and the solvent system in order to protect the adhesive layer until the patch is to be applied to the skin. Typical materials suitable for release liners are polyethylene and polyethylene-coated paper, preferably silicone-coated to facilitate removal.

Methods for preparing adhesive matrix transdermal devices are known in the art. A preferred method for preparing adhesive matrix transdermal devices of the present invention comprises casting a thin layer of the polymer blend onto the material to be used as the release liner, curing the polymer blend to form the polymer adhesive (including drying in an oven), and laminating the backing material to the resultant adhesive layer. Suitably sized patched may then be punched out automatically, and the patches are preferably sealed into protective pouches.

The layer of polymer blend cast on the release liner according to the preferred method is preferably about 5 mils to about 10 mils thick. The cast layer is preferably dried at a temperature of about 80° C. for a period of about 20 min. A specific example of a formulation is shown below.

Reservoir-type patches may also be made by known procedures. For example, a layer of adhesive may be applied to the release liner, the rate-controlling membrane may be laminated to the adhesive side, a portion of gelled estradiol solution may be placed on the membrane, and the backing material may then be heat-sealed to the rate-controlling membrane around the edges of the patch.

The side of the transdermal device of the present invention depends on the dose requirements, with preferred patch area being about 5 to about 20 cm$^2$, preferably 7.5 to 15 cm$^2$. The preferred delivery rate of estradiol is 0.25±0.2 ug/cm$^2$/hr, giving a preferred daily dosage of about 50 μg. A patch is applied and left in place for several days, preferably for 1 week, but shorter time periods, e.g 3 days or 1 day may also be used. The exact dose is predetermined by the skilled clinician depending on such factors as the age, weight and condition of the patient.

The following Table I shows typical adhesive matrix formulations of the present invention.

TABLE I
GENERAL FORMULATIONS

| INGREDIENT | FUNCTION | FORMULA 1 | FORMULA 2 | FORMULA 3 |
|---|---|---|---|---|
| Acrylic Pressure Sensitive Adhesive | Adhesive | 72.9% | — | 72.9% |
| Vinyl Acetate Pressure Sensitive Adhesive | Adhesive | — | 72.9% | — |
| Purified Water USP | Solvent | 8.7% | 8.7% | 8.7% |
| Dipropylene Glycol | Solvent | — | 5.3% | 2.5% |
| N-Methyl-2-pyrrolidone | Solvent | 5.3% | — | — |
| Estradiol | Drug | 1.1% | 1.1% | 1.1% |
| Ethanol USP | Processing Solvent | 5.3% | 5.3% | 5.3% |
| Ceraphyl-41 | Co-Solvent | 2.7% | 2.7% | 3.75% |
| Oleic Acid NF | Co-Solvent | 2.7% | 2.7% | 3.75% |
| Crosslinker | Crosslinker | 0.3% | 0.3% | 0.3% |
| Acrylic Polymer Thickener | Thickener | 1.0% or as needed to adjust viscosity. | 1.0% or as needed to adjust viscosity. | 1.0% or (q.s.) |

The following is a specific example of an adhesive matrix formation:

|  |  | Ingredients | Amount/100 g batch |
|---|---|---|---|
| Step I: | 1) | RA-2484 (or Flexbond 149) | 72.9 g |
|  | 2) | Aerotex Resin 3730 | 0.3 |
|  | 3) | Purified Water USP | 8.7 |
|  | 4) | Ceraphyl 41 | 2.7 |
|  | 5) | Dipropylene Glycol | 5.3 |
| Step II: | 1) | Oleic Acid | 2.7 |
|  | 2) | Ethanol | 5.3 |
|  | 3) | Estradiol | 1.1 |
|  | 4) | Thickener | 1.0 |
|  |  |  | 100.0 g |

12-pt. poly-coated paperboard (release liner) Volar foam (backing)

Add, in order, the ingredients for Step 1 and mix for 15 minutes. Separately combine, in order, the ingredients of Steps I and II and mix until smooth. Check viscosity, and if necessary, add thickener to increase viscosity of the polymer blend to the required level.

Cast a 5–10 mil layer of polymer blend onto the release liner. Dry the layer at 80° C. for 20 min. Laminate the backing material to the dry polymer film using conventional equipment.

Using an automatic punch machine, punch out the desired size patches. Using a pouch machine, enclose the patches in pouches and heat-seal closed.

Alternatively, in the above procedure the dipropylene glycol and ethanol may be interchanged, i.e., ethanol is mixed with the ingredients of Step I and dipropylene glycol is mixed with the ingredients of Step II.

The following Table II shows the in-vitro diffusion rates ($J_{SS}$=μg/cm$^2$/hr) of estradiol (E$_2$) from different transdermal patches through heat isolated human cadaver epidermis using single compartment diffusion cells.

TABLE II
IN-VITRO DIFFUSION RATES OF ESTRADIOL

| Formulation:* | | | | | | | |
|---|---|---|---|---|---|---|---|
| % E$_2$ | % m-p | % DPG | % C-41 | % OA | Adhesive | Study # | $J_{ss}$ (μg/cm$^2$/hr) |
| 2 | — | — | — | — | acrylic | 1 | 0.03 ± 0.01 |
| 2 | 15 | — | — | — | acrylic | 1 | 0.06 ± 0.03 |
| 2 | — | — | 15 | — | acrylic | 1 | 0.11 ± 0.02 |
| 2 | 10 | — | 5 | 5 | acrylic | 1 | 0.13 ± 0.02 |
| 2 | 10 | — | 5 | 5 |  | 2 | 0.12 ± 0.04 |
| 2 | 10 | — | 5 | 5 |  | 3 | 0.10 ± 0.02 |
| 2 | 10 | — | 5 | 5 |  | 4 | 0.17 ± 0.02 |
| 2 | 7.5 | — | 7.5 | 5 | acrylic | 1 | 0.13 ± 0.02 |
| 2 | 7.5 | — | 7.5 | 5 |  | 2 | 0.13 ± 0.03 |
| 2 | 7.5 | — | 7.5 | 5 |  | 3 | 0.13 ± 0.02 |
| 2 | — | 10 | 5 | 5 | vinyl-acetate | 1 | 0.26 ± 0.03 |
| 2 | — | 10 | 5 | 5 |  | 2 | 0.30 ± 0.17 |
| 2 | — | 10 | 5 | 5 |  | 3 | 0.21 ± 0.05 |
| 2 | — | 10 | 5 | 5 |  | 4 | 0.30 ± 0.04 |
| 2 | — | 10 | 5 | 5 |  | 5 | 0.33 ± 0.06 |
| 2 | — | 10 | 5 | 5 | acrylic | 1 | 0.29 ± 0.02 |
| 2 | — | 10 | 5 | 5 |  | 2 | 0.27 ± 0.03 |

*E$_2$ = estradiol;
m-p = m-pyrol;
C-41 = ceraphyl-41;
OA = oleic acid;
DPG = dipropylene glycol

We claim:

1. A pharmaceutical composition for use in an adhesive-matrix of reservoir transdermal device for transdermal delivery of estradiol or a pharmaceutically acceptable ester thereof comprising oleic acid, $D_{12}$–$C_{15}$ linear alcohol lactate and either dipropylene glycol or N-methyl-2-pyrrolidone.

2. A pharmaceutical composition of claim 1 for use in an adhesive-matrix further comprising a pharmaceutically acceptable pressure sensitive polymeric adhesive or adhesive mixture.

3. A pharmaceutical composition of claim 2 wherein the adhesive is selected from the group consisting of vinyl acetate, acrylic, silicone, synthetic or natural rubber latex pressure sensitive adhesives and mixtures thereof.

4. A pharmaceutical composition as defined in claim 2 comprising about 1 to about 10% estradiol or a pharmaceutically acceptable ester thereof, about 2.5 to about 5% oleic acid, about 2.5 to about 5% $C_{12}$–$C_{15}$ linear alcohol lactate, about 5 to about 10% dipropylene glycol or N-methyl-2-pyrrolidone.

5. A pharmaceutical composition of claim 4 further comprising about 0.1 to about 0.5% crosslinker and about 1 to about 2% thickener.

6. A polymer mixture suitable for preparing a pharmaceutical composition of claim 2 comprising about 0.5 to about 5% estradiol or a pharmaceutically acceptable ester thereof, about 1 to about 20% oleic acid, about 1 to about 10% $C_{12}-C_{15}$ linear alcohol lactate, about 1 to about 20% dipropylene glycol or N-methyl-2-pyrrolidone, and about 60 to about 80% pressure sensitive adhesive or adhesive mixture.

7. A polymer mixture of claim 6 comprising about 2 to about 5% oleic acid, about 1 to about 10% $C_{12}-C_{15}$ linear alcohol lactate, about 1 to about 20% dipropylene glycol or N-methyl-2-pyrrolidone, and about 60 to about 80% pressure sensitive adhesive or adhesive mixture.

8. A polymer mixture as defined in claim 6 further comprising about 0.1 to about 0.5% crosslinking agent, about 0.5 to about 1.5% thickener, about 5 to about 10% water, and about 2 to about 10% ethanol.

9. A polymer mixture of claim 8 comprising 72.9% pressure sensitive adhesive; 1.1% estradiol; 2.7 % $C_{12}-C_{15}$ linear alcohol lactate; 2.7% oleic acid; 0.3% crosslinking agent; 1.0% thickener; 8.7% water; 5.3% ethanol; and 5.3% dipropylene glycol or N-methyl-2-pyrrolidone.

10. A polymer mixture of claim 9 wherein the pressure sensitive adhesive is a vinyl acetate adhesive or an acrylic adhesive.

11. A pharmaceutical composition of claim 1 for use in a reservoir transdermal device comprising about 20 to about 60% dipropylene glycol or N-methyl-2-pyrrolidone; about 10 to about 40% oleic acid; about 10 to about 40% $C_{12}-C_{15}$ linear alcohol lactate; and about 5 to about 20% estradiol or a pharmaceutically acceptable ester thereof.

12. A pharmaceutical composition of claim 11 further comprising about 0.1 to about 2% gelling agent.

13. A process for preparing an adhesive matrix transdermal device for administering estradiol or a pharmaceutically acceptable ester thereof, said process comprising applying a polymer mixture to a backing member and curing the polymer mixture, wherein said polymer mixture comprises about 0.5 to about 5% estradiol or a pharmaceutically acceptable ester thereof, about 1 to about 20% oleic, about 1 to about 10% $C_{12}-C_{15}$ linear alcohol lactate, about 1 to about 20% dipropylene glycol or N-methyl-2-pyrrolidone, about 60 to about 80% pharmaceutically acceptable pressure sensitive adhesive or adhesive mixture, about 0.1 to about 0.5% crosslinking agent, about 0.5 to about 1.5% thickener, about 5 to about 10% water, and about 2 to about 10% ethanol.

* * * * *

UNITED STATES PATENT AND TRADEMARK OFFICE
CERTIFICATE OF CORRECTION

PATENT NO. : 5,154,922

DATED : October 13, 1992

INVENTOR(S) : Sharad K. Govil, et al.

It is certified that error appears in the above-identified patent and that said Letters Patent is hereby corrected as shown below:

column 6, line 45, delete "$D_{12}-C_{15}$" and insert instead --$C_{12}-C_{15}$-- column 6, line 62, after "N-methyl-2-pyrrolidone", insert--, and about 70 to about 90% pressure sensitive adhesive--.

Signed and Sealed this

Twenty-third Day of November, 1993

Attest:

BRUCE LEHMAN

*Attesting Officer*  *Commissioner of Patents and Trademarks*